United States Patent [19]
Fujieda et al.

[11] Patent Number: 5,532,772
[45] Date of Patent: Jul. 2, 1996

[54] OPHTHALMIC APPARATUS WITH POSITIONING CONTROL

[75] Inventors: Masanao Fujieda, Toyohashi; Nobuyuki Yano, Okazaki; Yoshiaki Mimura, Gamagori; Naoki Isogai, Nishio, all of Japan

[73] Assignee: Nidek Co., Ltd., Japan

[21] Appl. No.: 219,881

[22] Filed: Mar. 30, 1994

[30] Foreign Application Priority Data

Mar. 31, 1993 [JP] Japan ................................ 5-098938

[51] Int. Cl.$^6$ .................................................. A61B 3/10
[52] U.S. Cl. ........................... 351/211; 351/214; 351/221
[58] Field of Search .................................. 351/211, 221, 351/218, 214, 247, 212

[56] References Cited

U.S. PATENT DOCUMENTS 5,371,557  12/1994  Nanjho et al. .......................... 351/221

Primary Examiner—William L. Sikes
Assistant Examiner—Hung Xuan Dang
Attorney, Agent, or Firm—Finnegan, Henderson, Farabow, Garrett & Dunner

[57] ABSTRACT

An ophthalmic apparatus for use by an examiner in examining an examinee's eye includes an optical system for examining the examinee's eye, an observing optical path for observing the examinee's eye directly in binocular vision, a beam splitter disposed in the observing optical path, and a mark forming device for forming an aiming mark at a position conjugate to a predetermined portion of the anterior part of the eye, the light of the aiming mark being reflected by the light splitting member into the eyes of the examiner, wherein the positional relationship along the observing optical path between the anterior part of the examinee's eye and the aiming mark is perceived through the examiner's eyes and the suitability of the working distance of the apparatus can be judged.

14 Claims, 7 Drawing Sheets

OPHTHALMIC APPARATUS WITH POSITIONING CONTROL

BACKGROUND OF THE INVENTION

1. Field of the Invention

The present invention relates to an ophthalmic apparatus including an eye refractive power measurement apparatus and a cornea shape measurement apparatus and, more particularly, to an ophthalmic apparatus provided with an alignment system, particularly with a suitable constitution for accommodating a working distance of hand-held type apparatus.

2. Description of Related Art

Many ophthalmic apparatuses are installed-type apparatuses, which have conventional alignment system that an examiner directly observes an examinee's eye through an ocular lens-barrel to adjust the alignment of apparatus. The alignment system utilizes indexes projected onto the examinee's eye to detect suitability of the working distance. When the examinee's eye is positioned at a predetermined distance from the apparatus, images of indexes projected on the eye will coincides with each other. The alignment system has advantages in that it is relatively inexpensive and, because of a pure optical system, it enables observation of precision images within a range that resolving power of examinee's eye admits.

An ophthalmic apparatus which is provided with system of imaging an examinee's eye by infrared light and then displaying a visible image of the eye on a TV monitor, has come into wide use recently. In the ophthalmic apparatus, an optical axis adjusted by arranging an image of the examinee's eye, an alignment mark superimposed on the image of the eye and a first Purkinje image formed by a cornea reflection light so that they are positioned with a desired positional relation with each other, and a working distance is adjusted by bringing the first Purkinje image into focus. This alignment system has advantages in that it is not influenced by examiner's diopter, and the examiner can conduct alignment of the apparatus at a distance from the examinee's eye and in a comfortable position accordingly, and others.

In the former apparatus of conventional installed-type, the examinee and the examiner have to come close to each other, causing a problem of giving the examinee an uncomfortable feeling and compelling the examiner to take an unnatural position respectively.

The latter apparatus has also problems that it would be more expensive in cost and larger in size because it needs a television camera and a television monitor. And further, picture quality the latter apparatus provides is inferior than that of the former apparatus.

SUMMARY OF THE INVENTION

The present invention has been made in view of the above circumstances and has an object to overcome the above problems and to provide an ophthalmic apparatus of simple construction and with a proper aiming system.

Additional objects and advantages of the invention will be set forth in part in the description which follows and in part will be obvious from the description, or may be learned by practice of the invention. The objects and advantages of the invention may be realized and attained by means of the instrumentalities and combinations particularly pointed out in the appended claims.

To achieve the objects and in accordance with the purpose of the invention, as embodied and broadly described herein, an ophthalmic apparatus of this invention, which is for examining an examinee's eye in a state that the ophthalmic apparatus is positioned at a determined position, comprises measuring means including optical system for examining the examinee's eye, an observing optical path for observing the examinee's eye directly in binocular vision, a beam splitter disposed in the observing optical path, and mark forming means for forming an aiming mark at a position almost conjugate to a predetermined portion of the anterior part of the examinee's eye, and introducing a light of the aiming mark through said light splitting member into eyes of an examiner, whereby a positional relation along the observing optical path, before and behind, between the anterior part of the examinee's eye and the aiming mark is perceived by the examiner's eyes and suitability of a working distance is judged.

In the second aspect of the present invention, an ophthalmic apparatus, which is for examining an examinee's eye in a state that the ophthalmic apparatus is positioned at a determined position, comprises measuring means including optical system for examining the examinee's eye, an observing optical path for observing the examinee's eye in binocular vision, a beam splitter disposed in the observing optical path, mark forming means for forming an aiming mark image at a position almost conjugate to a predetermined portion of the anterior part of the eye, and introducing a light of the aiming mark through said light splitting member into eyes of an examiner, and cornea reflecting image forming means for projecting an image to be reflected by the cornea on the examinee's eye, whereby a positional relation along the observing optical path, before and behind, between the cornea reflecting image and the aiming mark is perceived by the examiner's eyes and suitability of a working distance is judged.

According to the present invention, adjusting system for working distance can be accomplished with very simple construction. By using the apparatus in accordance with the present invention, a distance in observing direction between an examiner and the apparatus can be freely determined and, accordingly, the examiner can measure in a comfortable position.

BRIEF DESCRIPTION OF THE DRAWINGS

The accompanying drawings, which are incorporated in and constitute a part of this specification illustrate an embodiment of the invention and, together with the description, serve to explain the objects, advantages and principles of the invention. In the drawings.

DETAILED DESCRIPTION OF THE PREFERRED EMBODIMENTS

A detailed description of one preferred embodiment of an ophthalmic apparatus embodying the present invention will now be given referring to the accompanying drawings.

Figure 1:
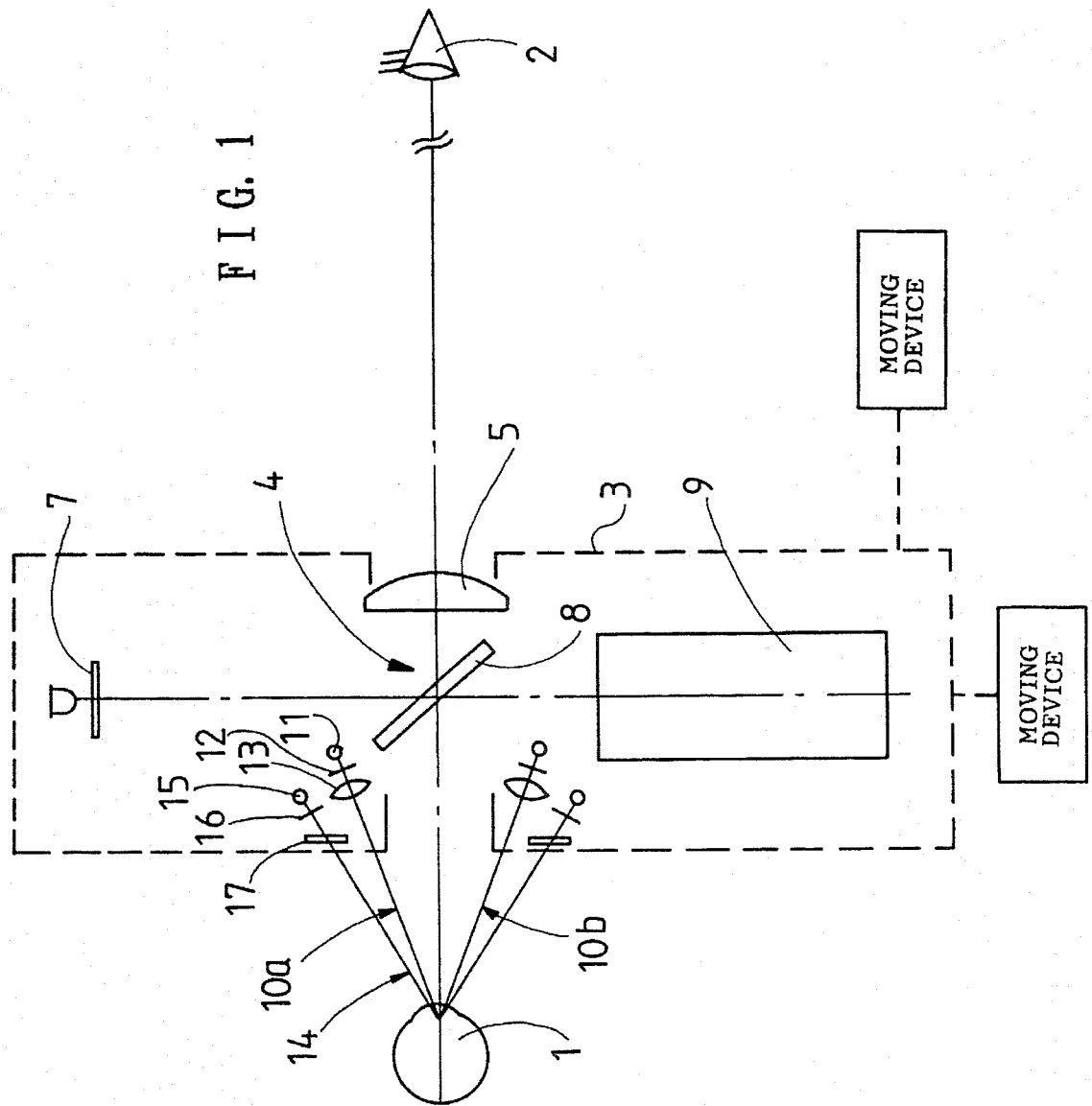
FIG. 1 is a schematic side view of an optical system of an apparatus in accordance with the present invention.
Figure 2:
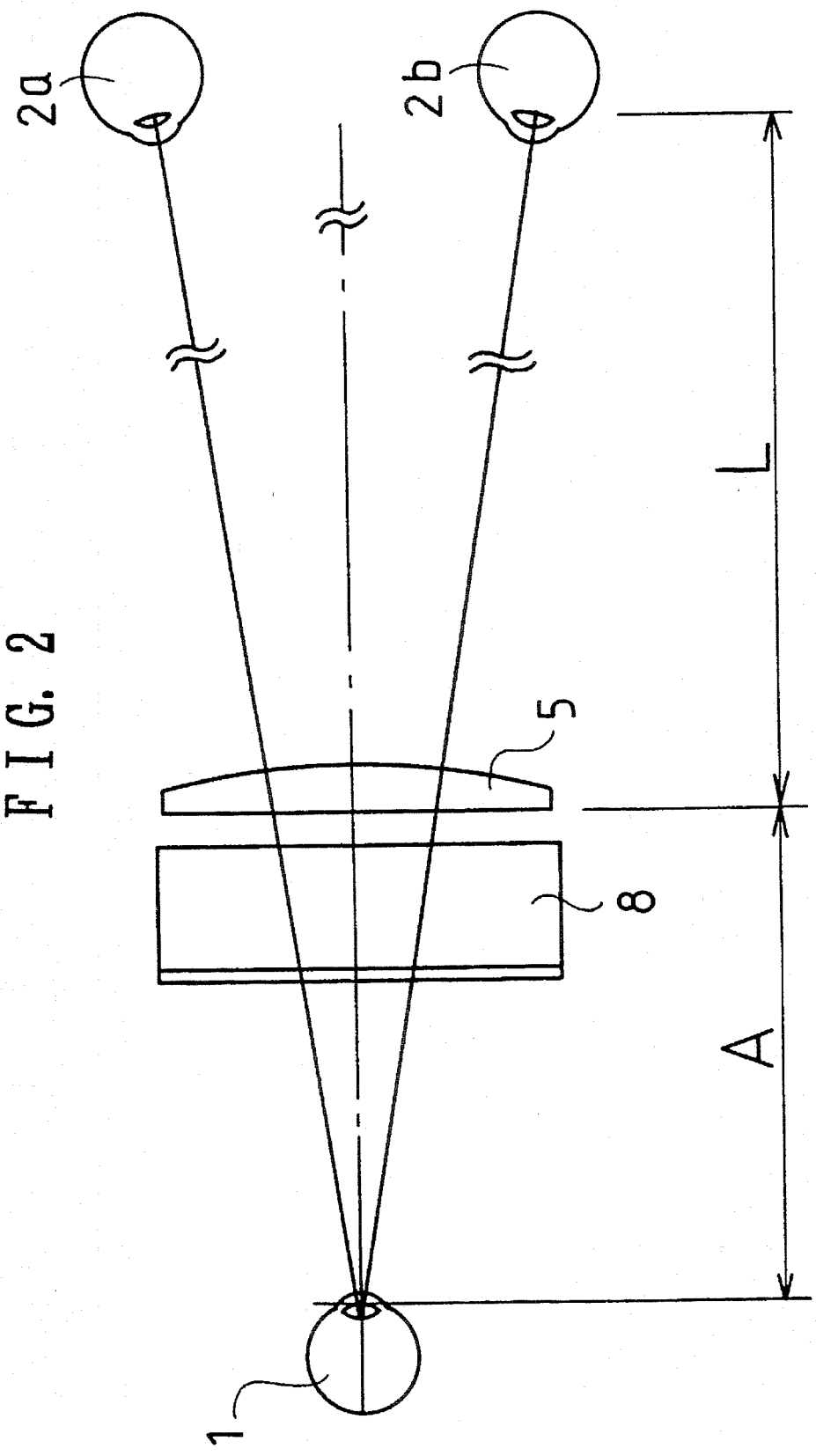
FIG. 2 is a schematic plane view of an observing system to an examinee's eye in FIG. 1.

FIG. 1 shows a side view of an optical system of the ophthalmic apparatus according to the present invention and FIG. 2 shows a plane view of an observing system for observing an examinee's eye.

Numeral 1 indicates an eye of an examinee and numeral 2 indicates an eye of an examiner respectively. In FIG. 1, the apparatus body 3, which is a cornea shape measurement apparatus of simplified type, is provided with a through hole 4 through which the examiner can observe the examinee's eye 1. The examiner's eyes 2a and 2b therefore observe the examinee's eye 1 through the objective lens 5 fitted in the through hole 4 in binocular vision. The objective lens 5 is for magnifying the examinee's eye 1. For example, in FIG. 2, if a distance (A) between the objective lens 5 and the examinee's eye 1 is 75 mm, a distance (L) between the objective lens 5 and the examiner's eye 2 is 200 mm and a focal distance (F) of the objective lens 5 is 250 mm, the examiner can then observe the magnified image of 1.28 times as large as the actual image. The apparatus body 3 is disposed so that a working distance between a measuring optical system mentioned later and the examinee's eye is proper when the apparatus body 3 is positioned at a determined distance from the iris of the examinee's eye 1. The working distance is determined on the basis of the iris of an examinee's eye (or a mire-ring image) in the present embodiment, and an outline of the cornea of the examinee's eye, that is, a borderline between the white part and the colored part of the eye seen in full face, may be utilized for the basis instead of the iris.

The apparatus body 3 is also provided with an illumination light source, an aiming mark plate 7, a beam splitter 8 arranged on the optical path of the observing system, a measuring device 9 and an index projecting optical system 10 for measuring the cornea shape of an examinee's eye.

Figure 3:
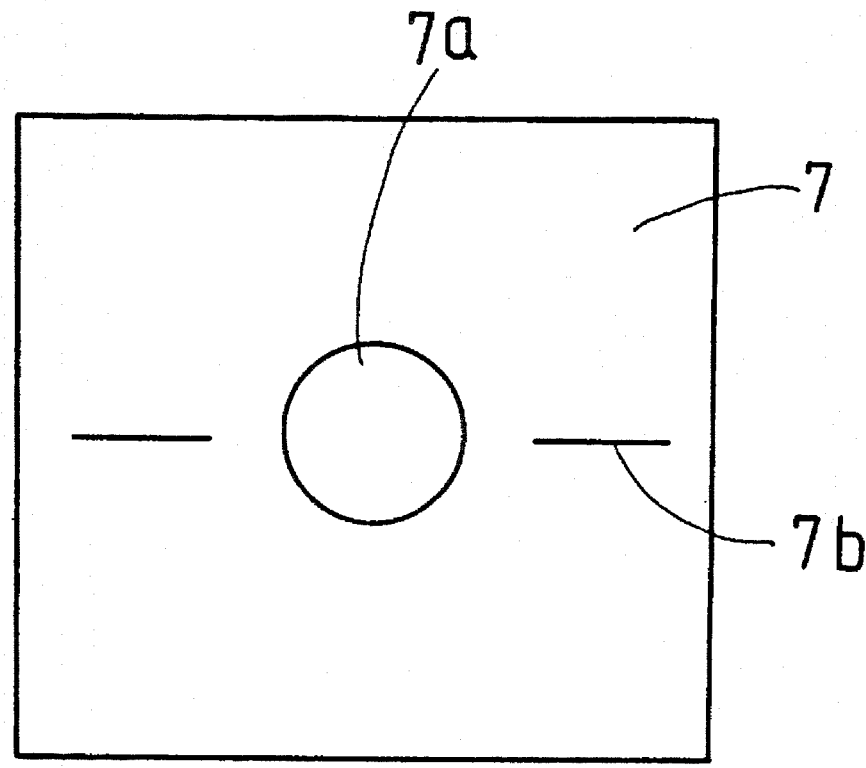
FIG. 3 is a diagram showing an aiming mark plate.

As shown in FIG. 3, the aiming mark plate 7 has slit apertures to form aiming marks 7a and 7b, specifically, an aiming mark 7a shows a ring pattern and another aiming mark 7b shows level reference line of the apparatus. The aiming mark 7b of level reference lines indicates 0 degrees direction of cornea astigmatism.

Light from the light source passes through each aperture of the aiming marks 7a and 7b provided in the aiming mark plate 7, and then mark light from the aiming mark plate 7 is reflected by the beam splitter 8 disposed in an observing optical path toward the examiner's eyes 2a and 2b. For the beam splitter 8, namely, a light splitting member, various transmitting/reflecting characteristics can be selected in consideration of optical characteristic of the light splitting member, wavelength of light forming aiming mark images, wavelength of measurement light, and wavelength of light forming a mire-ring image and the position of the same.

The measuring device 9 includes an optical system for measuring the cornea shape of an examinee's eye. Various known measuring optical systems can be utilized for the optical system, and the detailed explanation thereof is omitted herein. The measuring optical system is designed so that, when the examinee's eye 1 is positioned at a designed distance from an objective lens (not shown) of the measuring optical system, each optical path length from the beam splitter 8 to the aiming mark plate 7 and to the iris of examinee's eye 1 respectively may be equal.

The index projecting optical system 10 is consisted of four optical systems 10a–10d (10c and 10d are not shown in FIG. 1) arranged at 90-degrees angle apart from each other in a same circle centering the optical axis, each of which is constituted of a light source 11 for emitting light of infrared area, a spot diaphragm 12 and a collimator lens 13.

Mire-ring projecting optical system 14 is to form a mire-ring image on the examinee's eye, which is constituted of a light source 15 for emitting visible light, a diaphragm 16 with a ring-shaped aperture and a diffusing plate 17. Instead of forming mire-ring image, many point sources arranged in a same circle can be also useful to form a ring image as is shown in U.S. Pat. No. 5,463,430. A mire-ring image (Purkinje image) formed by the mire-ring projecting optical system 14 can be considered to be positioned near the fundus of the eye by almost half length of radius of curvature from the apex of cornea, the position being nearly correspondent to a position of the iris. Accordingly, the position of mire-ring image instead of the iris can be utilized for a reference position to detect whether the working distance is proper or not when the iris of the examinee's eye is not sufficiently visible due to poor light in an examination room, and so forth.

The procedures for adjusting the working distance in the apparatus constructed as above will be explained hereinafter.

Figure 4:
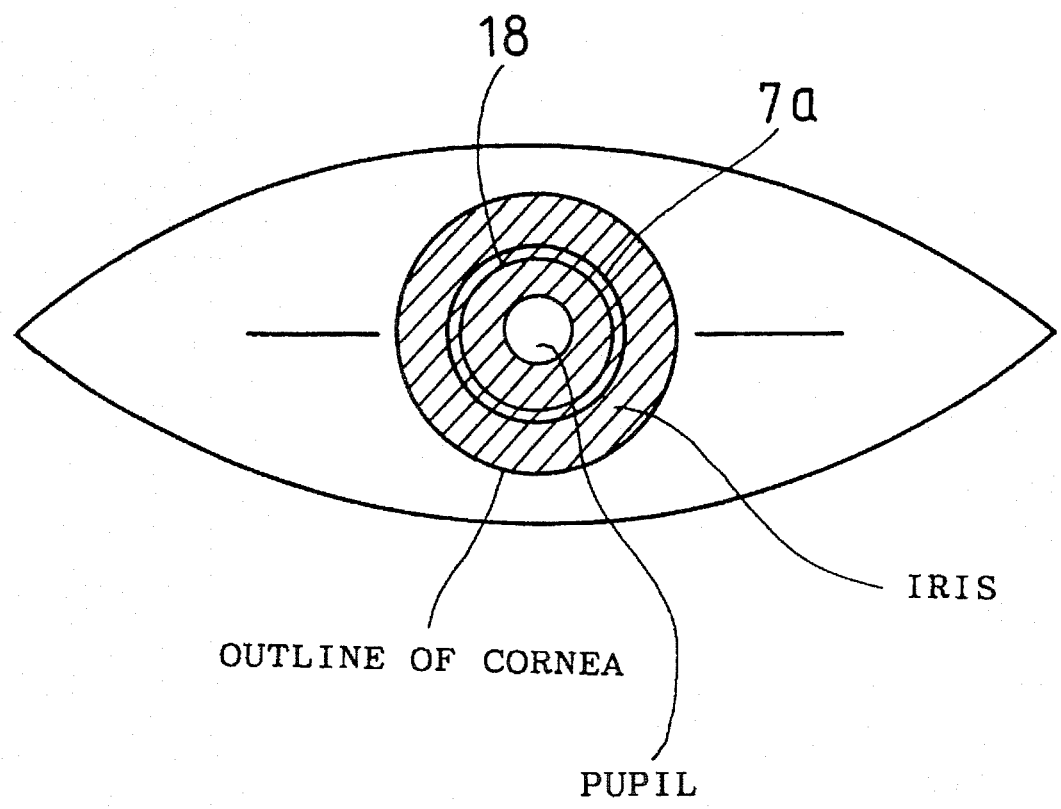
FIG. 4 is a diagram showing an observation image of the anterior part of the examinee's eye with a mire-ring image when the aiming mark plate in FIG. 3 is used.

The examiner first observes, with his both eyes 2a and 2b, the anterior part of the examinee's eye 1 through the objective lens 5 and the beam splitter 8, when the examiner simultaneously observes the aiming mark 7a of ring pattern through the beam splitter 8, which is superimposed on an image of the anterior part of the eye 1. FIG. 4 shows an example of an observed image of the eye when a mire-ring image 18 is also projected thereon. The mire-ring image 18 can also be utilized for positioning of the apparatus in up-and-down or right-and-left directions, that is, the examiner judges whether the mire-ring image 18 and the aiming mark 7a are positioned concentrically with each other, to adjust the positioning of the apparatus in vertical and horizontal directions. In a case where the iris is visible, the positioning of the apparatus can be conducted with the iris (or the mire-ring image) and the aiming mark 7a similarly.

The examiner judges suitability of the working distance based on the positional relation, before and behind, along the observing optical path between the iris of the examinee's eye 1 or the mire-ring image 18 and the aiming mark 7a, and the examiner moves the apparatus in a longitudinal direction so that the iris (or the mire-ring image) and the aiming mark 7a may be observed at a same distance to adjust the working distance.

The positional relation between the iris and the aiming mark 7a is detected as the following description.

Figure 5:
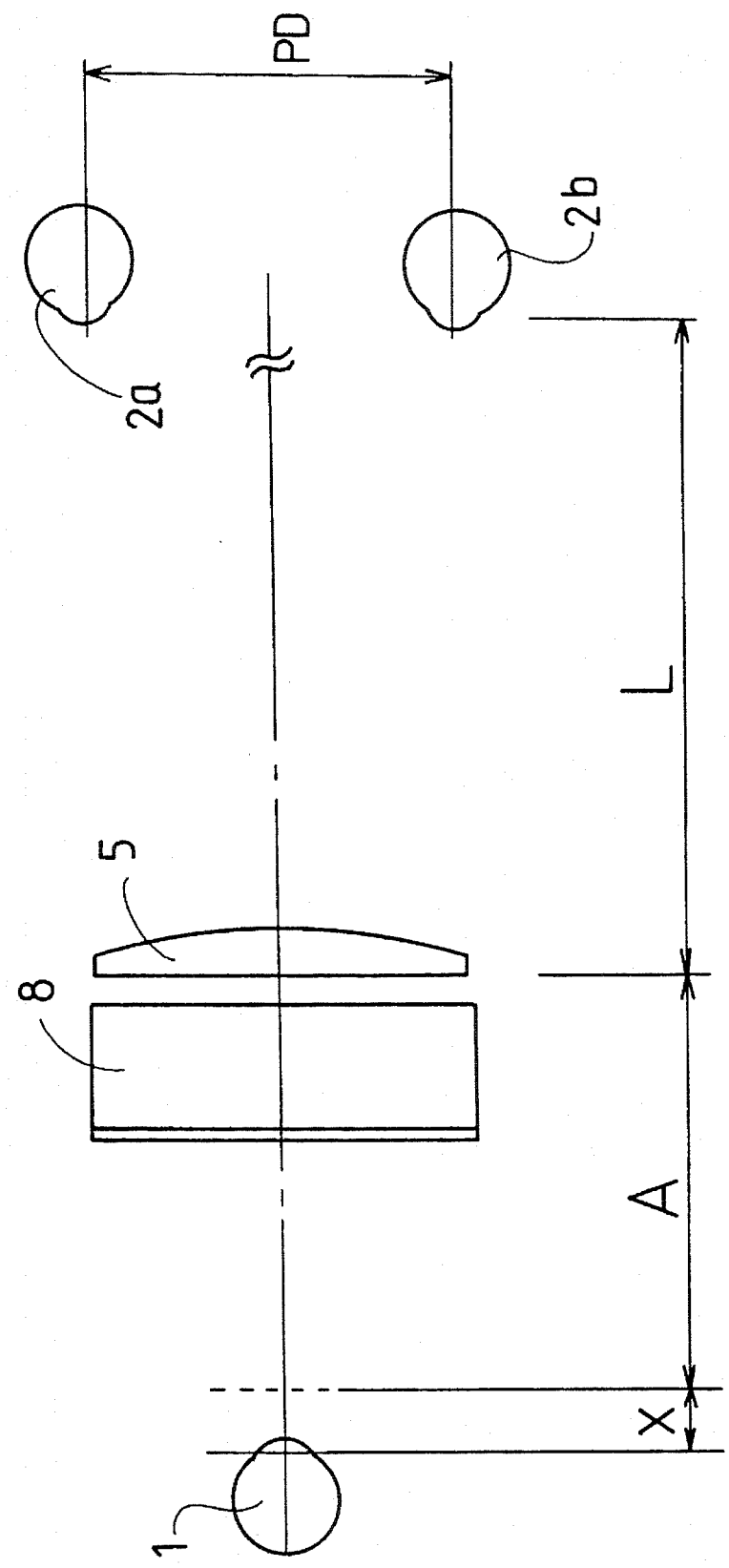
FIG. 5 is a schematic view showing a situation of the optical system when the image of the anterior part of the eye and the aiming mark are superimposed.

In a case where the anterior part of the eye 1 and the aiming mark 7a are superimposed, their positional relation can be showed in FIG. 5. In FIG. 5, "L" indicates distance from the examiner's eye 2 to the position of the objective lens 5, "A" indicates distance from the position of the objective lens 5 to the aiming mark 7a, "x" indicates distance difference between the aiming mark 7a and the iris of the eye 1, "PD" indicates interpupilary distance of the examiner's eyes, and "K" is a constant to transform radian to second as a unit.

When the objective lens 5 is not disposed in the observing optical path, stereoparallax "V" of the distance difference between the aiming mark 7a and the iris of the eye 1 is expressed by the following formula:

$$V=PD\cdot x\cdot K/(L+A)^2$$

Assuming that, for example, A is 75 mm, L is 200 mm, PD is 64 mm, x is 1 mm and K is 206265, the stereoparallax V is 174". It is said that depth perception of a person whose eyes are normal is generally around 30", the depth visual acuity which is a minimum value of stereoparallax whereby distance difference can be recognized, this means that the person can sufficiently detect distance difference even if it is about 1 mm.

Accordingly, when a convex lens is disposed as shown in FIG. 5, which is the objective lens 5 in the present embodiment, apparent stereoparallax based on the distance difference between the aiming mark 7a and the iris of the eye 1 can be magnified by the convex lens.

As previously mentioned, a convex lens having a focal length F=250 mm can form a magnified image of 1.28 times. Further, the convex lens also magnifies the distance difference between the aiming mark and the iris of the examinee's eye. Supposing the distance difference is "x'", it is given by the following formula.

$$x'=F\cdot(A+x)/(F-A-x)-F\cdot A/(F-A)$$

Stereoparallax "V" in this case is as follow.

$$V=PD\cdot x'\cdot K/[L+F\cdot A/(F-A)]^2$$

Calculating the above formulas, the stereoparallax V will be 287.2", as a result, it is found that stereoparallax can also be magnified.

Conversely, calculating back distance difference between the aiming mark and the iris of the examinee's eye, which is recognizable for a person who has normal eyes with depth visual acuity 30", the convex lens will enable the person to recognize a distance difference of 0.1 mm. Of course, it is practically sufficient if precision required for adjustment of working distance is lower, the precision must be determined properly in consideration of the influence of measurement items and construction of optical system on the precision of the working distance.

The examiner therefore judges suitability of the working distance based on the positional relation in a longitudinal direction between the iris of the examinee's eye 1 (or the mire-ring image) and the aiming mark 7a, and moves the apparatus in a longitudinal direction so that the iris (or the mire-ring image) and the aiming mark are observed at the same distance. The present invention utilizes an adjustment system for working distance based on the positional relation, therefore, the position of the examiner's eyes are relatively understricted and the examiner can observe at a distance easy of observation within the limits of accommodation of the examiner's eyes.

As described above, the examiner observes the positional relation in a longitudinal direction between the iris of the examinee's eye 1 (or the mire-ring image) and the aiming mark 7a, and depresses a measurement switch to measure optical characteristics of the examinee's eye 1 when the iris (or the mire-ring image) and the aiming mark 7a are observed at the same distance.

If it is difficult to clearly observe the iris due to poor light in an examination room, the positional relation is judged between the aiming mark 7a and a cornea reflection image of the mire-ring projecting optical system 14 instead of the iris. The cornea reflection image of the mire-ring projecting optical system 14 is positioned at an almost same position as the iris. Accordingly, even if measurement is conducted in the dark examination room, adjustment of the working distance can be done.

Figure 6:
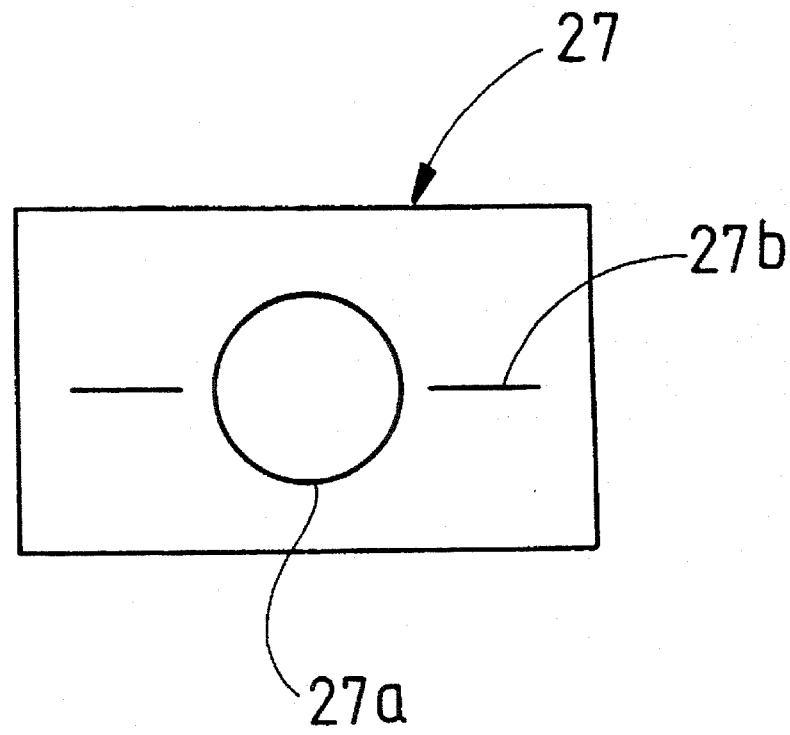
FIG. 6 is a diagram showing another example of aiming mark plate.
Figure 7:
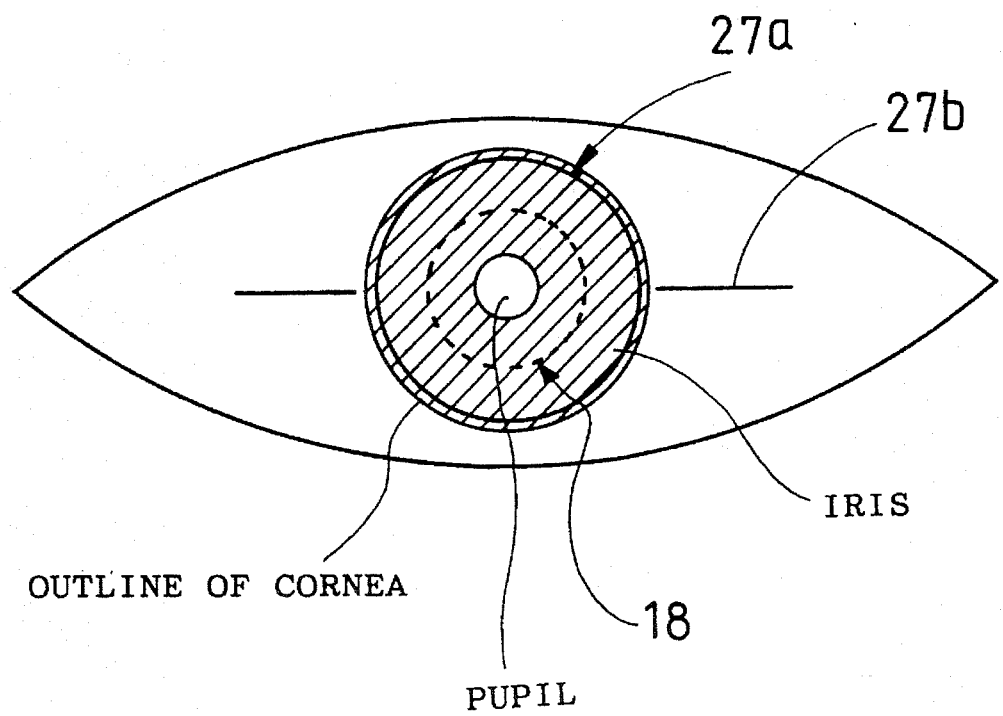
FIG. 7 is a diagram showing an observation image of the anterior part of the eye with a mire-ring image when the aiming mark shown in FIG. 6 is used.

FIG. 6 shows another embodiment of aiming mark plate. An aiming mark plate 27 is provided with aiming mark 27a which is approximately the same diameter (for instance, 12 mm in the present embodiment) as the outline of the cornea of when the examinee's eye is looked through the objective lens 5, and aiming mark 27b indicates level reference lines of the apparatus body. FIG. 7 shows an example of an observation image of when a mire-ring image is projected on the examinee's eye as is shown in U.S. Pat. No. 5,463,430. Also in this case, judging whether the outline of a cornea and the aiming mark 27a are positioned concentrically with each other can be utilized for positioning of the apparatus in up-and-down or right-and-left directions. And working distance is adjusted based on perceiving the positional relation between the iris (or the mire-ring image) and the aiming mark 27a.

The present invention may be embodied in other specific forms without departing from the spirit or essential characteristics thereof. Systems for moving the apparatus to the examinee's eye has not been described in detail in the above embodiment, because this takes hand-held type apparatus into consideration. The present invention is not, however, applied only to the hand-held type apparatus, can also be utilized for conventional apparatus of joystick type. The above embodiment adopts a method that the examiner depresses a measurement switch when the iris of the examinee's eye 1 and the aiming mark 7a are observed at a same distance, but it can utilize only an adjustment system for roughly adjusting the working distance. If adopting the method that the measurement switch must be depressed, hand-held type apparatus, particularly, may have inferior handling operation. It is therefore preferable in the hand-held type apparatus that rough alignment is conducted by utilizing the present invention, and the alignment condition is detected by alignment detecting system separately provided to give trigger signals. For the alignment detecting system, various known detecting systems can be used, and besides, the detecting system proposed in U.S. Pat. No. 5,463,430 by the present applicant can be used, the abstract thereof is as follows: apparatus for detecting alignment between an object to be examined having a refractive power and measurement system and others, in which projecting optical system for projecting a pair of indexes onto the object, the indexes having an optically different distance from the object, detecting optical system for detecting a pair of images of the indexes reflected from said object, and judging means for determining alignment condition based on the result detected by said detecting optical system.

The foregoing description of the preferred embodiment of the invention has been presented for purposes of illustration and description. It is not intended to be exhaustive or to limit the invention to the precise form disclosed, and modifications and variations are possible in light of the above teachings or may be acquired from practice of the invention. The embodiment chosen and described in order to explain the principles of the invention and its practical application to enable one skilled in the art to utilize the invention in various embodiments and with various modifications as are suited to the particular use contemplated. It is intended that the scope of the invention be defined by the claims appended hereto, and their equivalents.

What is claimed is:

1. An ophthalmic apparatus for use by an examiner in examining an examinee's eye where the ophthalmic apparatus is positioned at a determined position, the ophthalmic apparatus comprising:

measuring means including an optical system for examining the examinee's eye;

an observing optical path for observing the examinee's eye directly in binocular vision by the examiner;

a beam splitter disposed in the observing optical path; and mark forming means for forming an aiming mark at a position substantially conjugate to a predetermined portion of the anterior part of the eye, and introducing the aiming mark reflected by said beam splitter into the eyes of the examiner, wherein the positional relationship along the observing optical path between the anterior part of the examinee's eye and the aiming mark is perceived by the examiner's eyes and the suitability of a working distance can be judged.

2. An ophthalmic apparatus according to claim 1, further comprising a convex lens to magnify the anterior part of the examinee's eye in said observing optical path.

3. An ophthalmic apparatus according to claim 1, wherein said mark forming means includes an illuminating light source and an aiming mark forming plate, and light passed through said mark forming plate is reflected by said beam splitter toward the examiner's eyes.

4. An ophthalmic apparatus according to claim 1, wherein said measuring means includes a cornea shape measurement apparatus or an eye refracting power measurement apparatus.

5. An ophthalmic apparatus according to claim 1, wherein the aiming mark provided by said mark forming means includes a ring-shaped image.

6. An ophthalmic apparatus according to claim 5 wherein the aiming mark further includes level reference lines.

7. An ophthalmic apparatus according to claim 1 wherein said aiming mark is a ring in shape, and any positional deviation of the apparatus body in up-and-down and right-and-left directions is judged based on whether said aiming mark and the iris or an outline of the cornea are positioned concentrically with each other.

8. An ophthalmic apparatus for use by an examiner in examining an examinee's eye where the ophthalmic apparatus is positioned at a determined position, the ophthalmic apparatus comprising:

measuring means including an optical system for examining the examinee's eye;

an observing optical path for observing the examinee's eye in binocular vision by the examiner;

a beam splitter disposed in the observing optical path;

mark forming means for forming an aiming mark at a position substantially conjugate to a predetermined portion of the anterior part of the eye, and introducing the aiming mark reflected by said beam splitter into the eyes of the examiner; and cornea reflecting image forming means for projecting an image to be reflected by the cornea on the examinee's eye, wherein the positional relationship along the observing optical path between the cornea reflecting image and the aiming mark is perceived by the examiner's eyes and the suitability of a working distance can be judged.

9. An ophthalmic apparatus according to claim 8, further comprising a convex lens to magnify the anterior part of the examinee's eye in said observing optical path.

10. An ophthalmic apparatus according to claim 8, wherein said cornea reflecting image forming means includes mire-ring image forming means for projecting a mire-ring image on the examinee's eye.

11. An ophthalmic apparatus according to claim 10, wherein said mire-ring image forming means includes a projecting optical system for projecting a ring slit image on the examinee's eye.

12. An ophthalmic apparatus according to claim 10, wherein said mire-ring image forming means includes a projecting optical system for projecting images of plural points arranged in a circle on the examinee's eye.

13. An ophthalmic apparatus according to claim 10, wherein said aiming mark is a ring in shape, and any positional deviation of the apparatus body in up-and-down and right-and-left directions is judged based on whether said aiming mark and said mire-ring image are positioned concentrically with each other.

14. An ophthalmic apparatus according to claim 8, wherein the aiming mark provided by said mark forming means is a ring-shaped image.

\* \* \* \* \*